United States Patent [19]

Yokozuka

[11] Patent Number: 4,919,142

[45] Date of Patent: Apr. 24, 1990

[54] MECHANISM FOR OPENING AND CLOSING MERCURY SPHYGMOMANOMETER

[75] Inventor: Tsuchiyasu Yokozuka, Fujioka, Japan

[73] Assignee: Yamasu Co., Ltd., Saitama, Japan

[21] Appl. No.: 293,409

[22] Filed: Jan. 4, 1989

[30] Foreign Application Priority Data

Aug. 31, 1988 [JP] Japan .................. 63-217569

[51] Int. Cl.[5] .............................................. A61B 5/02
[52] U.S. Cl. .................................................. 128/684
[58] Field of Search .................. 128/672, 677–686; 73/747–748; 251/231, 235, 286–288

[56] References Cited

U.S. PATENT DOCUMENTS

| | | | | |
|---|---|---|---|---|
| 1,134,632 | 4/1915 | Nicholson | .......................... | 73/748 X |
| 3,316,766 | 5/1967 | Jones | .................................. | 128/684 X |
| 4,073,314 | 2/1978 | Speelman et al. | ............... | 251/288 X |
| 4,090,503 | 5/1978 | Speidel | ............................... | 73/748 X |
| 4,173,328 | 11/1979 | Karbo | ............................... | 251/288 X |

Primary Examiner—Angela D. Sykes
Attorney, Agent, or Firm—Armstrong, Nikaido, Marmelstein, Kubovcik & Murray

[57] ABSTRACT

A mechanism for opening and closing a mercury sphygmomanometer having a set of blood pressure measuring means mounted on the inner side of a cover pivotally attached to a casing and a lever actuated in response to an operation of pivoting the cover such that the lever selects an opening or closing position of a valve provided in between a mercury passage and a mercury reservoir in response to an operation of pivoting the cover. The lever is provided with two abutments which are disposed in a predetermined angular relation to each other with respect to the pivot point of the lever. One of the abutments is movable by a manual operation to select a valve opening or closing position.

3 Claims, 4 Drawing Sheets

MECHANISM FOR OPENING AND CLOSING MERCURY SPHYGMOMANOMETER

BACKGROUND OF THE INVENTION

The present invention relates to a mechanism for opening and closing a mercury sphygmomanometer. More particularly, the present invention pertains to a mercury sphygmomanometer opening and closing mechanism whereby a valve which is attached to a mercury passage is automatically opened and closed in response to an operation of opening and closing a cover for the apparatus.

A typical conventional mercury sphygmomanometer will be briefly described hereinunder with reference to FIG. 5.

Referring to FIG. 5, a mercury passage 1 is connected to a mercury reservoir 2 through a communicating tube 3. The tube 3 is provided with a cock 4 which is opened and closed by means of a handle 5.

A cuff, or wrapping sleeve, 6 is connected to the mercury reservoir 2 through a tube 7 and also connected to a bulb 9 through a tube 8. The mercury passage 1 is provided at its upper end with a filter 10 and a small bore 11 through which the mercury passage 1 is communicated with the outside air. The reference numeral 12 denotes mercury contained in the mercury reservoir 2.

In actual use, the cuff 6 is wrapped around the arm and, with the cock 4 opened, air is pumped into the cuff 6 by means of the bulb 9. In consequence, the mercury 12 in the mercury reservoir 2 rises through the mercury passage 1, thus enabling measurement of blood pressure.

After the use, the mercury passage 1 is tilted to return all the mercury remaining in the passage 1 to the mercury reservoir 2 and then the cock 4 is closed in order to prevent leakage and contamination of the mercury 12.

There is another type of conventional mercury sphygmomanometer having an arrangement in which a cover is formed together with the mercury passage in one unit so that, as the cover is closed, the cock is automatically closed.

Of the above-described conventional apparatuses, the former has the disadvantage that the cock must be opened and closed every time the sphygmomanometer is used and put away in the casing. The latter, that is, the prior art wherein the cock is automatically opened and closed in response to to an operation of opening and closing the cover, suffers from the disadvantage that the operational relationship between the cover and the cock is fixed such that, when the cover is open, the cock is open, whereas, when the cover is closed, the cock is closed.

SUMMARY OF THE INVENTION

In view of the above-described circumstances, it is a primary object of the present invention to provide a mechanism for opening and closing a mercury sphygmomanometer which is designed so that the cock is automatically closed in response to an operation of closing the cover and it is also possible to select a cock opening or closing position as desired by a manual operation even when the cover is open.

To this end, the present invention provides a mechanism for opening and closing a mercury sphygmomanometer having a set of blood pressure measuring means mounted on the inner side of a cover pivotally attached to a casing and a lever actuated in response to an operation of pivoting the cover such that the lever selects an opening or closing position of a valve provided in between a mercury passage and a mercury reservoir in response to an operation of pivoting the cover, wherein the lever is provided with two abutments which are disposed in a predetermined angular relation to each other with respect to the pivot point of the lever, one of the abutments being movable by a manual operation to select a valve opening or closing position.

Thus, in normal use, the valve is automatically opened and closed in response to an operation of opening and closing the cover. At the time of maintenance or the like, the valve is opened and closed as desired by turning the lever by a manual operation.

DESCRIPTION OF THE PREFERRED EMBODIMENT

One embodiment of the present invention will be described hereinunder with reference to the accompanying drawings.

Figure 1:
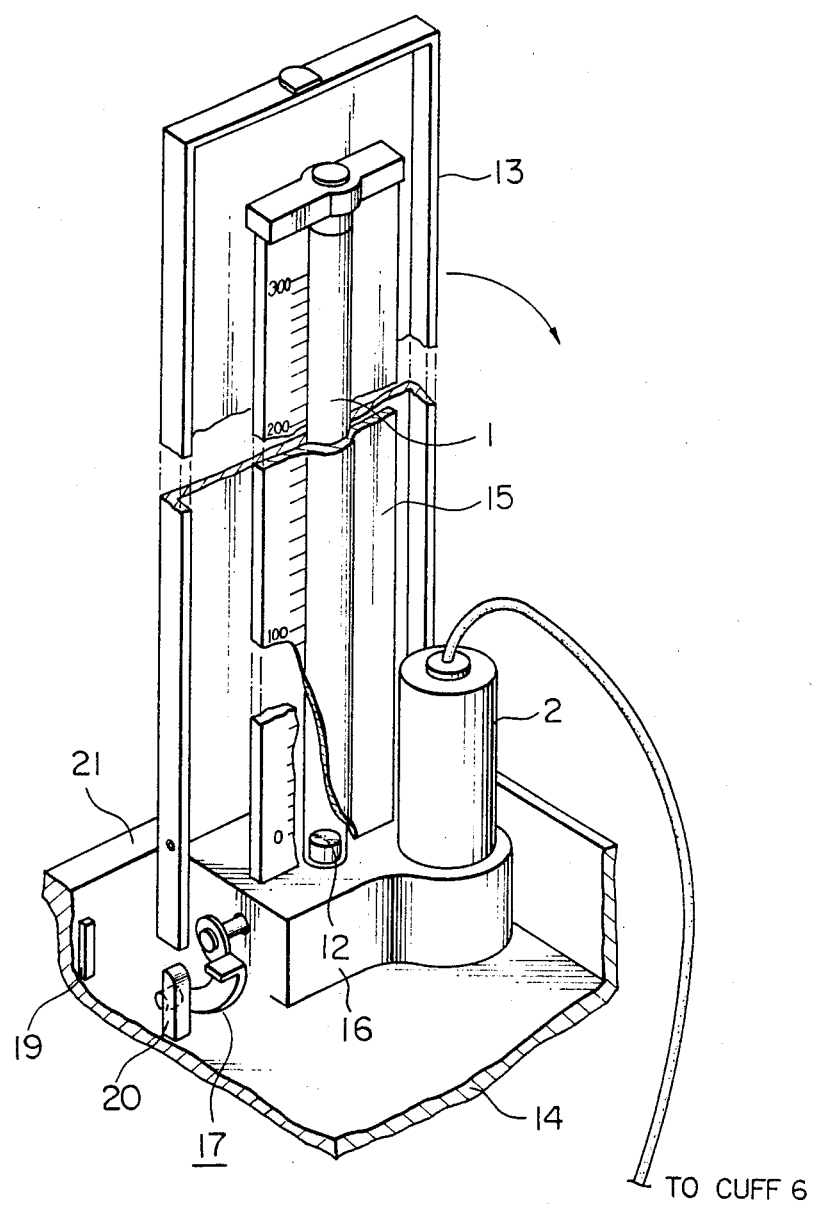
FIG. 1 is a perspective view of one embodiment of the mechanism for opening and closing a mercury sphygmomanometer according to the present invention.
Figure 2:
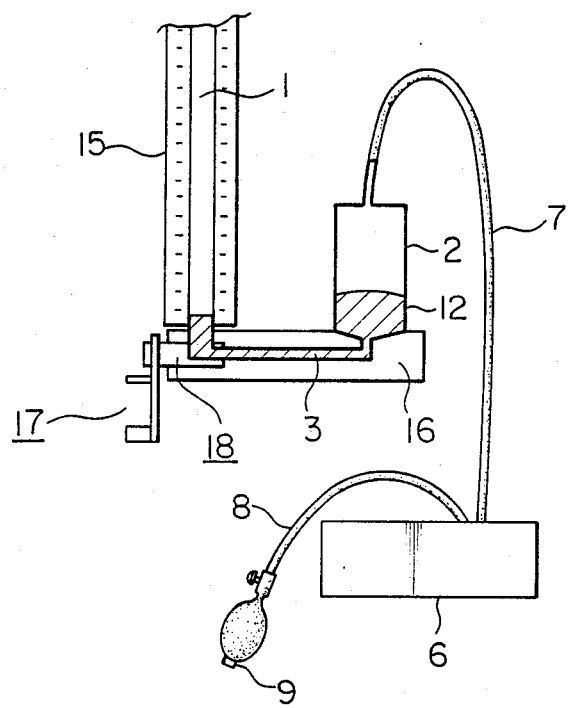
FIG. 2 shows the connection relationship between the elements that constitute in combination the arrangement shown in FIG. 1 in terms of the passage of air.

FIG. 1 is a partially-cutaway perspective view showing the general arrangement of one embodiment of the mercury sphygmomanometer opening and closing mechanism according to the present invention, while FIG. 2 shows the connection relationship between the elements that constitute in combination the arrangement shown in FIG. 1 in terms of the passage of air.

Figure 5:
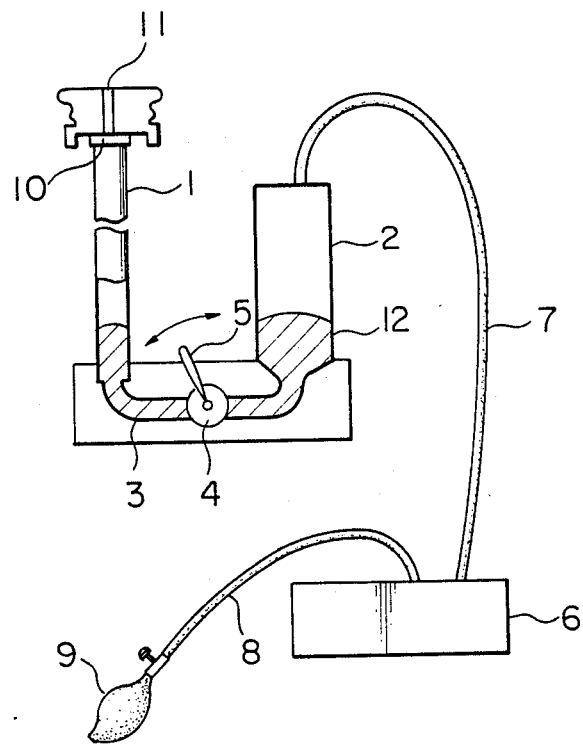
FIG. 5 is a partially-sectioned schematic view showing a conventional mercury sphygmomanometer.

First, the general arrangement of the mercury sphygmomanometer will be briefly described with reference to FIGS. 1 and 2 in which the same elements as those shown in FIG. 5 are denoted by the same reference numerals. A cover 13 is pivotally attached to a casing 14 so that the cover 13 is capable of pivoting in the direction of the solid-line arrow to close the casing 14. A mercury passage 1 is disposed in the center of the cover 13. A calibration plate 15 is attached in such a manner as to support the mercury passage 1. A base 16 is provided at the lower end of the cover 13. The mercury passage 1 and a mercury reservoir 2, which are mounted on the upper side of the base 16, are connected to each other through a communicating tube 3 inside the base 16 (see FIG. 2).

The reference numeral 17 denotes a lever for opening and closing a valve 18. A projection 19 is provided on one end of the casing 14 such that the projection 19 abuts against the lever 17 and causes it to pivot (described later). The reference numeral 20 denotes an abutment piece. It should be noted that the reference numeral 21 in FIG. 1 denotes the pivot shaft position about which the cover 13 pivots.

The arrangement of the lever 17 will next be explained with reference to FIG. 3.

Figure 3:
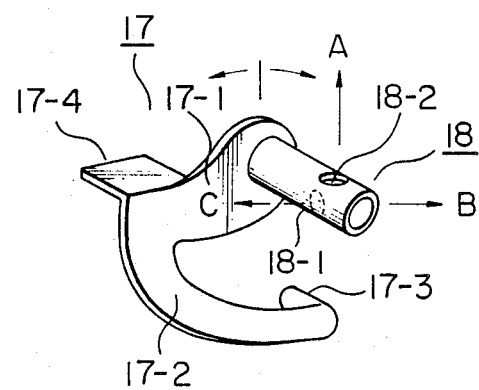
FIG. 3 shows the arrangement of the lever employed in the embodiment.

FIG. 3 shows the lever 17 in a perspective view for the purpose of facilitating understanding of the arrangement. The lever 17 comprises an actuating arm 17-1 rigidly secured to a shaft 18-1, a swing arm 17-2 formed integral with the actuating arm 17-1, an abutment (stopper) 17-3 projecting from the distal end of the swing arm 17-2, and an abutment (actuating plate) 17-4 formed integral with the actuating arm 17-1 so as to project therefrom in the shape of a flat plate. It should be noted that the shaft 18-1 has a bore 18-2 provided in the side wall thereof. Thus, the opening and closing operation of the valve 18 is achieved by the change in the direction of the bore 18-2 which is caused by the rotation of the shaft 18-1 which is, in turn, caused by the pivotal motion of the lever 17.

More specifically, when the apparatus is used with the cover 13 opened upright as shown in FIG. 1, the lever 17 is in the position shown in FIG. 3, that is, the bore 18-2 provided in the shaft 18-1 faces upward. Accordingly, the mercury passage 1 and the communicating tube 3 are communicated with each other to allow the mercury 12 to move in the mercury passage 1. This is the open position (the direction of the arrow (A) of the valve 18. When the lever 17 is pivoted 90° either clockwise or counterclockwise, the bore 18-2 faces sideward to shut off the mercury passage 1. This is the closed position (the direction of the arrow B or C) of the valve 18.

Figure 4:
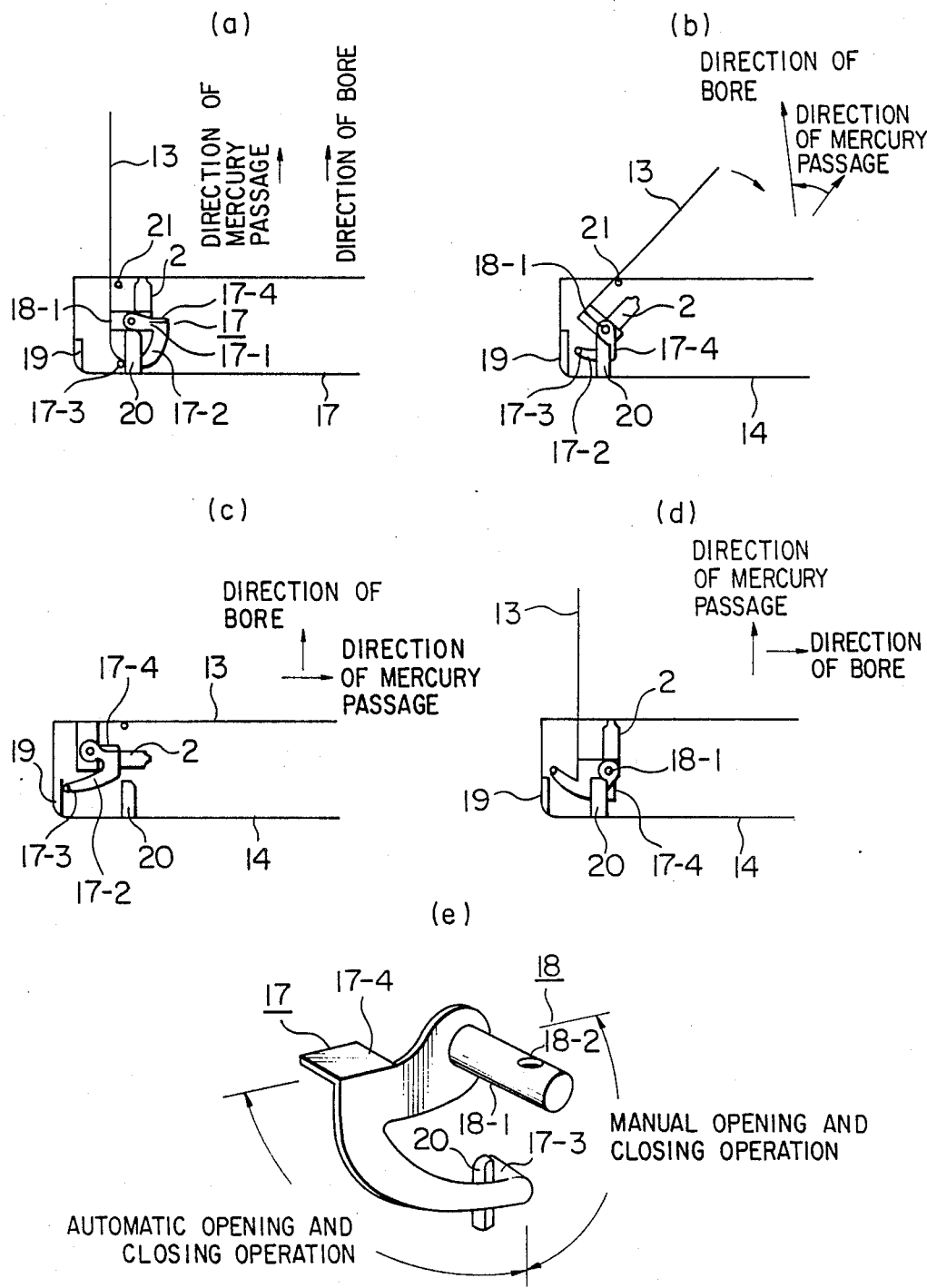
FIG. 4 is an exploded view showing the operation of the embodiment.

The operation of this embodiment will be sequentially explained hereinunder with reference to FIG. 4 which shows the opening and closing mechanism in a schematic view for the purpose of facilitating understanding of the operation.

(1) FIG. 4(a) shows the apparatus which is in use with the cover 13 opened upright. In this state, the constituent elements are in the illustrated positional relationship.

More specifically, when the cover 13 which is in its closed position is pivoted about the shaft position 21 in the direction of the solid-line arrow shown in the figure, the lever 17 pivots in the same direction about the shaft 18-1 until the abutment (stopper) 17-3 comes into contact with the abutment piece 20. At this time, the bore 18-2 in the shaft 18-1, which is at 90° with respect to the mercury passage 1 when the cover 13 is closed, is moved through 90° by the operation of opening the cover 13, so that the bore 18-2 and the mercury passage 1 are aligned with each other to bring the apparatus into an operative state.

(2) FIG. 2(b) shows the apparatus which is in a state wherein the cover 13 is in the process of being pivoted in the closing direction. In this process, the abutment (actuating plate) 17-4 once comes into contact with the abutment piece 20 (until the former contacts the latter, the relative positional relationship between the lever 17 and the mercury passage 1 is the same as in the case where the cover 13 is open) and, on contacting the abutment piece 20, the lever 17 causes the shaft 18-1 to pivot counterclockwise relative to the cover 13. At this time, the abutment (stopper) 17-3 has not yet come into contact with the projection 19. As the cover 13 is further pivoted in the closing direction, the abutment (actuating plate) 17-4 rotates counterclockwise relative to the cover 13 around the axis of the shaft 18-1 and, while doing so, it slides on the top portion of the abutment piece 20. When the abutment (actuating plate) 17-4 separates from the top portion of the abutment piece 20, the abutment (stopper) 17-3 comes into contact with the projection 19 instead. Even when the abutment (stopper) 17-3 is in contact with the projection 19, the cover 13 can be further pivoted in the closing direction. At this time, however, the pivotal motion of the cover 13 causes the shaft 18-1 to rotate counterclockwise relative to the cover 13, so that, when the cover 13 is fully closed as shown in FIG. 4(c), the bore 18-2 is at 90° with respect to the mercury passage 1 and thus the valve 18 is in its closed position.

(3) FIG. 4(d) is a view employed to describe an operation of closing the valve 18 which may be carried out when the apparatus is in use with the cover 13 opened upright.

Since the apparatus is in an operative state, the positional relationship between the constituent elements is the same as that shown in FIG. 4(a). More specifically, the abutment (stopper) 17-3 is in contact with the abutment piece 20 and therefore cannot rotate counterclockwise. However, the abutment (actuating plate) 17-4 can be pushed down so as to rotate through 90° in the clockwise direction. More specifically, the abutment (actuating plate) 17-4 can be rotated clockwise around the axis of the shaft 18-1 until it comes into contact with the abutment piece 20, that is, the abutment (actuating plate) 17-4 is movable within an angle range of 90°. Accordingly, the direction of the bore 18-2 can be changed so as to be at 90° with respect to the mercury passage 1 to close the valve 18. It should be noted that, if the cover 13 is closed in this state, the valve 18 is once opened (i.e., communicated with the mercury passage (1) and then closed.

As will be clear from the foregoing description, it is also possible to close the valve with the cover left open and this is considerably advantageous at the time of replacement of glass tubes and maintenance of the apparatus.

As has been described above, the present invention enables the valve to be automatically opened and closed in response to an operation of opening and closing the cover and also permits the valve to be opened and closed by a manual operation even when the cover is open. Thus, it is possible to provide a mechanism for opening and closing a mercury sphygmomanometer which enables the apparatus to be conveniently used with an increased degree of freedom and which also facilitates the maintenance.

What we claim is:

1. A mercury sphygmomanometer having a set of blood pressure measuring means mounted on the inner side of a cover pivotally attached to a cover of a casing and a lever actuated in response to an operation of pivoting said cover such that said lever selects an opening or closing position of a valve provided in between a mercury passage and a mercury reservoir in response to a operation of pivoting said cover, said lever comprising:

means for opening and closing said valve which has two abutments provided on said lever, said two abutments being disposed in a predetermined angular relation to each other with respect to the pivot point of said lever, one of said abutments being movable by a manual operation to select a valve opening or closing position.

2. In a mercury sphygmomanometer for measuring blood pressure mounted in a casiug which has a pivotally attached cover, a unitary device for controlling the flow of mercury between a mercury passage and a mercury reservoir in response to opening or closing said cover comprising:
- a rotary valve between said passage and said reservoir, and having an open and a closed position; and
- a lever attached to said valve having two abutment members disposed in a predetermined angular relation to each other with respect to the pivot point of said lever,
- one of said abutment members being movable by a manual operation to select a valve open or closed position.

3. A mercury sphygmomanometer comprising:
a casing;
a cover pivotally attached to said casing and having an inner side;
blood pressure measuring means mounted on said inner side and including:
- a mercury reservoir,
- a mercury passage connected to said reservoir,
- a rotary valve between said reservoir and said passage and having a closed and an open position,
- a lever attached to said valve; and
- means for actuating said lever upon opening and closing of said cover to open and close said valve, said actuating means including:
    - two abutment members disposed in a predetermined angular relation to each other with respect to the pivot point of said lever,
- one of said abutment members being movable by a manual operation to select a valve open or closed position.

* * * * *